United States Patent
Ito et al.

(10) Patent No.: US 9,304,078 B2
(45) Date of Patent: Apr. 5, 2016

(54) ELECTRON GUN ABNORMALITY DETECTING DEVICE AND ELECTRON GUN ABNORMALITY DETECTING METHOD

(71) Applicant: JFE STEEL CORPORATION, Tokyo (JP)

(72) Inventors: Tomohiko Ito, Tokyo (JP); Junichi Yotsuji, Tokyo (JP); Shigehiro Takajo, Tokyo (JP); Hiroi Yamaguchi, Tokyo (JP); Kazuhiro Hanazawa, Tokyo (JP); Yasunari Koga, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 14/431,221

(22) PCT Filed: Sep. 25, 2013

(86) PCT No.: PCT/JP2013/075942
§ 371 (c)(1),
(2) Date: Mar. 25, 2015

(87) PCT Pub. No.: WO2014/050906
PCT Pub. Date: Apr. 3, 2014

(65) Prior Publication Data
US 2015/0241335 A1 Aug. 27, 2015

(30) Foreign Application Priority Data
Sep. 28, 2012 (JP) .................................. 2012-216381

(51) Int. Cl.
*G01J 4/00* (2006.01)
*G01N 21/21* (2006.01)
*G01R 33/032* (2006.01)
*H01J 29/48* (2006.01)

(52) U.S. Cl.
CPC .............. *G01N 21/21* (2013.01); *G01R 33/032* (2013.01); *H01J 29/48* (2013.01); *G01N 2201/062* (2013.01)

(58) Field of Classification Search
CPC ........................................................... G01J 4/00
USPC ........................................................... 356/364
See application file for complete search history.

(56) References Cited

U.S. PATENT DOCUMENTS

| | | | | |
|---|---|---|---|---|
| 2013/0130043 A1* | 5/2013 | Omura | ................ | C21D 8/1255 428/450 |
| 2015/0253242 A1* | 9/2015 | Ito | .......................... | G01N 21/86 148/121 |

FOREIGN PATENT DOCUMENTS

| | | | |
|---|---|---|---|
| JP | S59180355 A | | 10/1984 |
| JP | S62102103 A | | 5/1987 |

(Continued)

OTHER PUBLICATIONS

Mar. 4, 2014 Office Action issued in Japanese Application No. 2012-216381.

(Continued)

*Primary Examiner* — Roy M Punnoose
(74) *Attorney, Agent, or Firm* — Oliff PLC (57) ABSTRACT

An electron gun abnormality detecting device for detecting an abnormality in first and second electron guns of a magnetic domain refining device for an electrical steel sheet includes: a magnetooptic element configured to contact with and separate from an inspection region set to include a boundary between a magnetic domain discontinuity generated by irradiation of a surface of the electrical steel sheet with an electron beam by the first electron gun and a magnetic domain discontinuity generated by irradiation thereof with an electron beam by the second electron gun, and configured to detect a steel sheet magnetic domain structure in the inspection region as an optical property; a light source configured to irradiate the magnetooptic element with linearly polarized light; and a detector configured to detect polarized light rotated by the steel sheet magnetic domain structure transferred to the magnetooptic element.

21 Claims, 8 Drawing Sheets

(56) References Cited

FOREIGN PATENT DOCUMENTS

| JP | H05119130 A | 5/1993 |
|---|---|---|
| JP | 2002257718 A | 9/2002 |
| JP | 2007101519 A | 4/2007 |
| JP | 2012031519 A | 2/2012 |
| JP | 2012035288 A | 2/2012 |
| JP | 2012052230 A | 3/2012 |

OTHER PUBLICATIONS

Feb. 24, 2012 Office Action issued in Japanese Application No. 2012-216381.
Dec. 3, 2013 International Search Report issued in International Application No. PCT/JP2013/075942.
Mar. 4, 2013 Office Action issued in Japanese Application No. 2012-216381.

* cited by examiner

ROLLING DIRECTION

ELECTRON GUN ABNORMALITY DETECTING DEVICE AND ELECTRON GUN ABNORMALITY DETECTING METHOD

FIELD

The present invention relates to an electron gun abnormality detecting device and an electron gun abnormality detecting method.

BACKGROUND

Electrical steel sheets are steel sheets having excellent magnetic properties with high magnetic permeability and small core loss. For example, grain oriented electrical steel sheets are often used in cores of transformers. Alternating current flowing through an electric wire wound around a core of a transformer generates an alternating magnetic field inside the core. In general, if an alternating magnetic field is applied in a steel sheet, eddy current loss and hysteresis loss are generated. Electrical steel sheets are demanded to have such eddy current loss and hysteresis loss reduced therein.

The generation of eddy current loss upon the application of an alternating magnetic field to a steel sheet is unavoidable, and the greater the frequency is, the greater the eddy current loss will be. However, a width of a magnetic domain of a steel sheet is one factor influencing this eddy current loss, and the narrower this width is, the more the eddy current loss is able to be reduced. Thus, magnetic properties of a steel sheet and a shape of the magnetic domain are known to be very deeply related to each other.

Accordingly, in a manufacturing process of grain oriented electrical steel sheets, in order to reduce the eddy current loss, a method of refining magnetic domains (magnetic domain refining process) is performed. A magnetic domain of a grain oriented electrical steel sheet extends in a rolling direction, and by adding a strain or forming a groove in a direction intersecting this magnetic domain, the magnetic domain is able to be refined (for example, see Patent Literature 1). A method of giving a thermal strain by irradiation with, for example, laser, electron beams, or the like, in the direction intersecting the magnetic domain, is known as a method of adding the strain. A technique is known, which is for observing a magnetic domain structure in order to inspect whether or not this magnetic domain refining process has been performed appropriately (see Patent Literature 2).

CITATION LIST

Patent Literature

Patent Literature 1: Japanese Patent Application Laid-open No. 2012-052230
Patent Literature 2: Japanese Patent Application Laid-open No. 2007-101519

SUMMARY

Technical Problem

However, in the magnetic domain refining process, due to a factor, such as deterioration of the filament of the electron gun that generates the electron beam, the magnetic domain refining process may not be performed as prescribed. Further, by conventional inspection techniques, a magnetic domain structure of a steel sheet subjected to the magnetic domain refining process is not able to be detected immediately after the magnetic domain refining process, and the steel sheet needs to be separately sampled for inspection offline. For example, in the inspection technique described in Patent Literature 2, time is needed for the magnetic powder to move through the solution and form an image reflecting the magnetic domain structure. Therefore, even if a problem occurs in the magnetic domain refining process, since a long period of time is required until that problem is detected, the yield is reduced due to nonconforming products being continuously manufactured.

The present invention has been made in view of the above, and an object thereof is to provide an electron gun abnormality detecting device and an electron gun abnormality detecting method, which are able to detect, by inspection at inspection points less than the number of installed electron guns of a magnetic domain refining device, an abnormality in the electron guns.

Solution to Problem

To solve the above-described problem and achieve the object, an electron gun abnormality detecting device according to the present invention detects an abnormality in electron guns of a magnetic domain refining device for an electrical steel sheet, the magnetic domain refining device including at least a first electron gun and a second electron gun, and includes: a magnetooptic element configured to contact with and separate from an inspection region set to include a boundary between a magnetic domain discontinuity generated by irradiation of a surface of the electrical steel sheet with an electron beam by the first electron gun and a magnetic domain discontinuity generated by irradiation thereof with an electron beam by the second electron gun, and configured to detect a steel sheet magnetic domain structure in the inspection region as an optical property; a light source configured to irradiate the magnetooptic element with linearly polarized light; and a detector configured to detect polarized light rotated by the steel sheet magnetic domain structure transferred to the magnetooptic element.

To solve the above-described problem and achieve the object, an electron gun abnormality detecting method according to the present invention detects an abnormality in electron guns of a magnetic domain refining device including at least a first electron gun and a second electron gun, and includes: a contacting step of contacting, with a steel sheet, a magnetooptic element that detects a magnetic domain structure of the steel sheet as an optical property at an inspection region set to include a boundary between a magnetic domain discontinuity generated by irradiation with an electron beam by the first electron gun and a magnetic domain discontinuity generated by irradiation with an electron beam by the second electron gun; an irradiating step of irradiating the magnetooptic element with linearly polarized light; a detecting step of detecting a rotation of a polarization plane of the linearly polarized light reflected by the magnetooptic element; a measuring step of measuring the magnetic domain structure of the steel sheet from the rotation of the polarization plane; and a separating step of separating the magnetooptic element from the steel sheet.

Advantageous Effects of Invention

An electron gun abnormality detecting device and an electron gun abnormality detecting method according to the present invention achieve an effect of being able to detect, by inspection at inspection points less than the number of installed electron guns of a magnetic domain refining device, an abnormality in the electron guns.

DESCRIPTION OF EMBODIMENTS

Hereinafter, an electron gun abnormality detecting device and an electron gun abnormality detecting method according to an embodiment of the present invention will be described in detail based on the drawings. The present invention is not limited by the embodiment described below.

[Electron Gun Abnormality Detecting Device]

Figure 1:
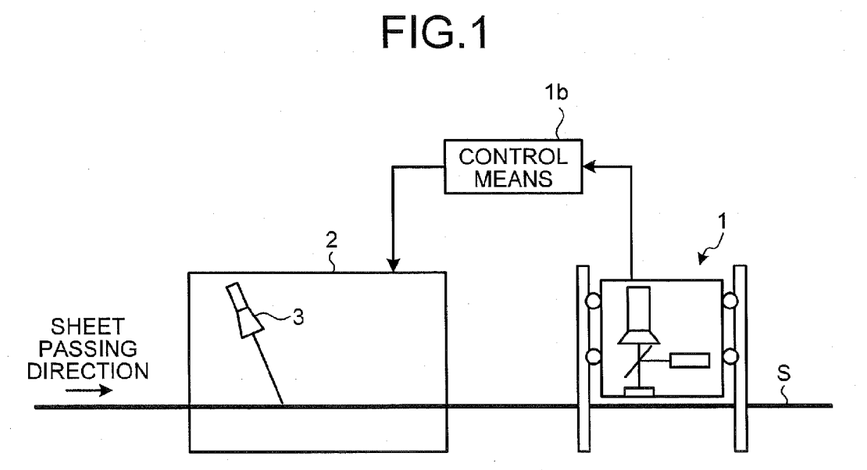
FIG. 1 is a block diagram illustrating a manufacturing line including an electron gun abnormality detecting device according to an embodiment of the present invention.

FIG. 1 is a block diagram illustrating a manufacturing line including an electron gun abnormality detecting device 1 according to an embodiment of the present invention. As illustrated in FIG. 1, the electron gun abnormality detecting device 1 according to the embodiment of the present invention is arranged at a rear stage of a magnetic domain refining device 2 that performs a magnetic domain refining process on a steel sheet "S". The magnetic domain refining device 2 is a device that includes electron guns 3 therein and gives a strain in a direction intersecting a magnetic domain of the steel sheet "S" by irradiating the steel sheet "S" with electron beams from the electron guns 3.

The magnetic domain refining device 2 performs the magnetic domain refining process on a surface of the steel sheet "S" and the electron gun abnormality detecting device 1 inspects the surface of the steel sheet "S" subjected to the magnetic domain refining process by the magnetic domain refining device 2. Based on a result of the inspection by the electron gun abnormality detecting device 1, a control means 1b determines an abnormality in the electron guns 3 of the magnetic domain refining device 2, and as necessary, controls the electron guns 3. The control means 1b may be an automatic control device, such as a PLC, or manual control by an operator.

Figure 2:
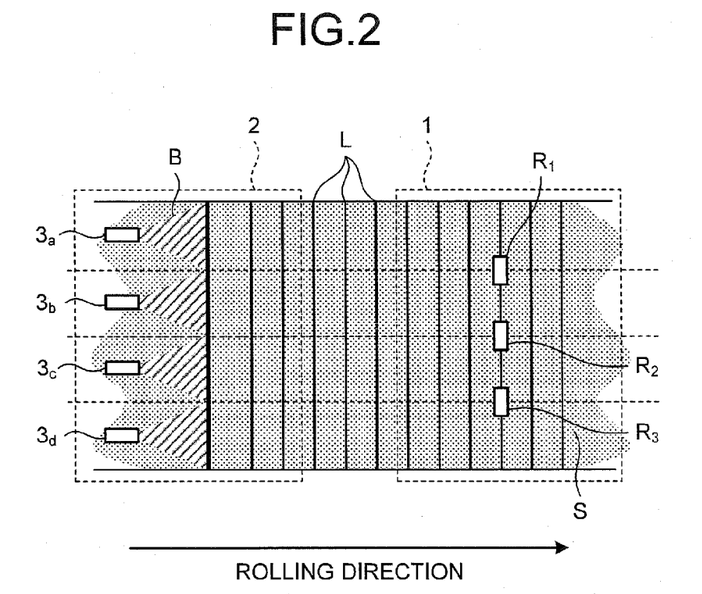
FIG. 2 is a schematic diagram illustrating a scheme of detecting an abnormality in electron guns, according to the embodiment of the present invention.

FIG. 2 is a schematic diagram illustrating a scheme of detecting an abnormality in electron guns, according to the embodiment of the present invention. As illustrated in FIG. 2, the magnetic domain refining device 2 includes a plurality of electron guns $3_a$, $3_b$, $3_c$, and $3_d$. The magnetic domain refining device 2 illustrated in FIG. 2 includes the four electron guns $3_a$, $3_b$, $3_c$, and $3_d$, but the present invention is also applicable to a magnetic domain refining device 2 including more electron guns. The present invention is applicable to a magnetic domain refining device 2 including at least two or more electron guns.

The plurality of electron guns $3_a$, $3_b$, $3_c$, and $3_d$ irradiate the surface of the steel sheet "S" in a width direction with straight-lined electron beams "B" in corporation with one another. That is, when the plurality of electron guns $3_a$, $3_b$, $3_c$, and $3_d$ add a straight lined strain intersecting a magnetic domain and in the width direction of the steel sheet "S", a straight line in this width direction is divided and the respective electron guns $3_a$, $3_b$, $3_c$, and $3_d$ irradiate the divided straight line with the electron beams "B". The magnetic domain refining device 2 illustrated in FIG. 2 includes the four electron guns $3_a$, $3_b$, $3_c$, and $3_d$ in a straight line, but a configuration is also possible, in which the four electron guns $3_a$, $3_b$, $3_c$, and $3_d$ are placed in a so-called staggered arrangement and by the timing to perform irradiation with the electron beams "B" being controlled, the four electron guns $3_a$, $3_b$, $3_c$, and $3_d$ irradiate the surface of the steel sheet "S" with the straight-lined electron beams "B" in the width direction in corporation with one another.

On the surface of the steel sheet "S" irradiated with the electron beams or laser as described above, closure domain dividing a main magnetic domain that is along a rolling direction is formed. Hereinafter, the closure domain formed on the surface of the steel sheet "S" that has been irradiated with the electron beams or laser will be referred to as magnetic domain discontinuity "L".

The steel sheet "S" processed by the plurality of electron guns $3_a$, $3_b$, $3_c$, and $3_d$ as described above is inspected by the electron gun abnormality detecting device 1 at the rear stage. That is, the electron gun abnormality detecting device 1 inspects whether or not the magnetic domain discontinuity "L" formed by the plurality of electron guns $3_a$, $3_b$, $3_c$, and $3_d$ is of a desired processed result.

As described above, the magnetic domain discontinuity "L" is irradiated with the electron beams by being divided plurally in relation to the width direction of the steel sheet "S". Therefore, the electron gun abnormality detecting device 1 performs inspection at a boundary of each division in the magnetic domain discontinuity "L".

In the schematic diagram illustrated in FIG. 2, an inspection region of the electron gun abnormality detecting device 1 at a boundary between the magnetic domain discontinuity "L" generated by the electron gun $3_a$ and the magnetic domain discontinuity "L" generated by the electron gun $3_b$ is $R_1$, an inspection region of the electron gun abnormality detecting device 1 at a boundary between the magnetic domain discontinuity "L" generated by the electron gun $3_b$ and the magnetic domain discontinuity "L" generated by the electron gun $3_c$ is $R_2$, and an inspection area of the electron gun abnormality detecting device 1 at a boundary between the magnetic domain discontinuity "L" generated by the electron gun $3_c$ and the magnetic domain discontinuity "L" generated by the electron gun $3_d$ is $R_3$.

Figure 3:
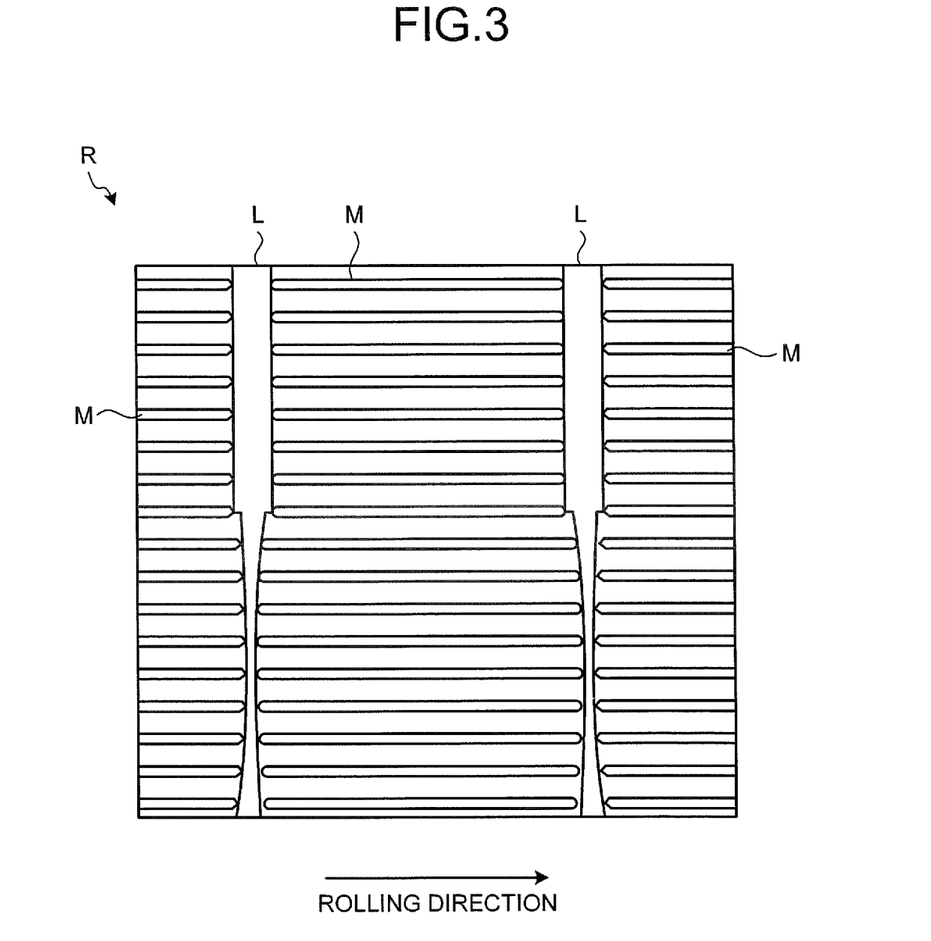
FIG. 3 is a schematic diagram of an inspection image when an abnormality of an electron gun is detected in an inspection region.
Figure 4:
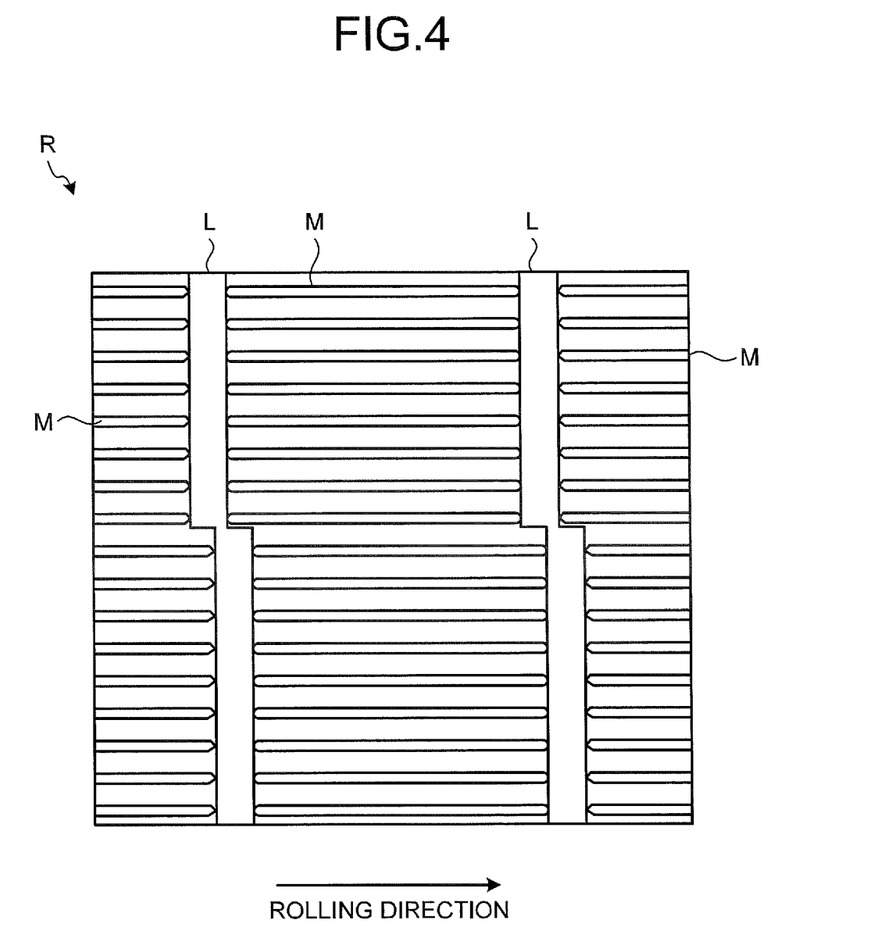
FIG. 4 is a schematic diagram of an inspection image when an abnormality in an electron gun is detected in an inspection region.

FIG. 3 and FIG. 4 are schematic diagrams of inspection images when an abnormality in the electron guns 3 is detected in an inspection area R. As illustrated in FIG. 3 and FIG. 4, on the surface of the steel sheet "S" subjected to the magnetic domain refining process by the magnetic domain refining device 2, magnetic domain discontinuities "L" are formed. Further, between the magnetic domain discontinuities "L", main magnetic domains "M" aligned along the rolling direction are formed.

As illustrated in FIG. 3, the electron gun abnormality detecting device 1 may obtain an inspection result with the magnetic domain discontinuity "L" of the top half of the inspection region "R" and the magnetic domain discontinuity "L" of the bottom half of the inspection region "R" having different widths. If an inspection result as illustrated in FIG. 3 is obtained, the filament of the electron gun 3 that has irradiated the magnetic domain discontinuity "L" having the narrowed width with the electron beam is considered to have deteriorated.

As illustrated in FIG. 4, the electron gun abnormality detecting device 1 may obtain an inspection result with the magnetic domain discontinuity "L" of the top half of the inspection area "R" and the magnetic domain discontinuity "L" of the bottom half of the inspection area "R" being displaced from each other. If an inspection result as illustrated in FIG. 4 is obtained, mechanical displacement of the electron gun 3 or deviation in timing to emit the electron beam from the electron gun 3 is considered to have been caused.

As illustrated in FIG. FIG. 3 and FIG. 4, the electron gun abnormality detecting device 1 according to the embodiment of the present invention performs the inspection at the boundaries of the respective divisions in the magnetic domain discontinuity "L", and thus two electron guns 3 of the electron guns 3 of the magnetic domain refining device 2 are able to be inspected simultaneously for abnormality. Therefore, the electron gun abnormality detecting device 1 according to the embodiment of the present invention is able to detect an abnormality in the electron guns 3 by inspection at inspection points less than the number of electron guns 3 installed in the magnetic domain refining device 2.

Hereinafter, with reference to FIG. 5 to FIG. 8, a specific configuration of the electron gun abnormality detecting device 1 according to the embodiment of the present invention will be described.

Figure 5:
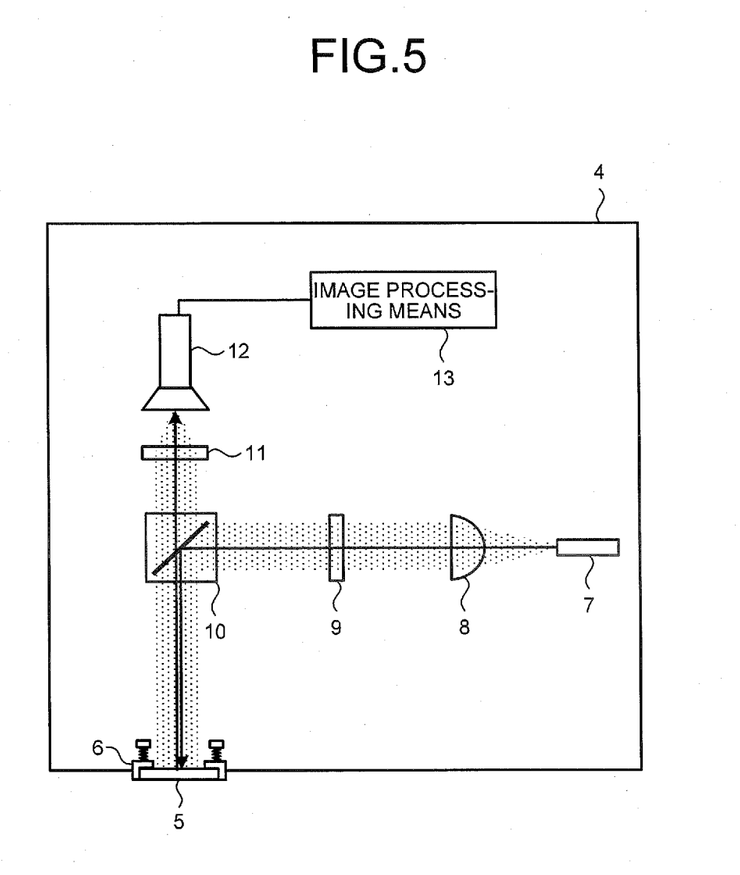
FIG. 5 is a schematic diagram illustrating an example of an internal configuration of an inspection unit of the electron gun abnormality detecting device.

FIG. 5 is a schematic diagram illustrating an example of an internal configuration of an inspection unit 4 of the electron gun abnormality detecting device 1. The electron gun abnormality detecting device 1 is a device that comes into contact with the steel sheet "S" and inspects the electron guns 3 for abnormality by the inspection unit 4 being driven when the manufacturing line is temporarily stopped.

As illustrated in FIG. 5, the inspection unit 4 includes a magnetooptic element 5 that converts a magnetic domain structure of the steel sheet "S" into an optical property, a holder 6 that fixes the magnetooptic element 5 to the inspection unit 4 via an elastic body, and an incident-light optical system that irradiates the magnetooptic element 5 with linearly polarized light and detects reflected polarized light reflected from the magnetooptic element 5. That is, the inspection unit 4 includes, as the incident-light optical system, a light source 7, a collimator lens 8, a polarizer (polarizing filter) 9, a half mirror 10, an analyzer (polarizing filter) 11, and a detector 12.

The magnetooptic element 5 is an element that converts the magnetic domain structure of the steel sheet "S" into an optical property by a magnetooptic effect called Faraday effect. Faraday effect is an effect of a polarization plane rotating by a magnetic field felt by a substance when linearly polarized light is transmitted through the substance, and an example of a representative substance achieving this Faraday effect is magnetic garnet. More specifically, iron garnet substituted with Bi is able to be used.

By the inspection unit 4 being driven, the magnetooptic element 5 comes into contact with the inspection region "R" of the steel sheet "S", the magnetic domain structure of the steel sheet "S" is transferred to the magnetooptic element 5, and the polarization plane of polarized light, with which the magnetooptic element 5 is irradiated, is rotated. The holder 6 fixes the magnetooptic element 5 to the inspection unit 4 via the elastic body in order to relieve the impact when the inspection unit 4 is driven to contact the magnetooptic element 5 with the steel sheet "S".

The light source 7 is for irradiating the magnetooptic element 5 with linearly polarized light, and for example, a general light source, such as a semiconductor laser light source or an LED light source, is used. The light source 7 does not need to be a light source that emits polarized light directly, and generates, in combination with the polarizer (polarizing filter) 9, linearly polarized light, with which the magnetooptic element 5 is irradiated. Further, the light source 7 is used in combination with an optical element, such as the collimator lens 8, so that polarized light is able to be emitted as parallel light. For example, if a green LED light source (wavelength of 505 nm) is used, the contrast is improved.

The polarizer 9 is a polarizing filter that converts light rays emitted from the light source 7 into linearly polarized light. The polarizer 9 adjusts polarized light detected by the detector 12 by adjusting a relative angle thereof with the analyzer 11. That is, the polarizer 9 has a rotation mechanism and is able to adjust an angle of the polarization plane of the linearly polarized light. If the analyzer 11 has the rotation mechanism, the rotation mechanism in the polarizer 9 may be omitted.

The half mirror 10 is an optical path dividing means that guides the linearly polarized light transmitted through the polarizer 9 to the magnetooptic element 5 and guides the reflected polarized light reflected from the magnetooptic element 5 to the detector 12. The analyzer 11 adjusts polarized light detected by the detector 12 by adjusting a relative angle thereof with the above described polarizer 9. The detector 12 is a general two-dimensional image acquiring device, such as a so-called CCD camera or CMOS camera. An image detected by the detector 12 is subjected to appropriate image processing by a separate image processing means 13, such as a PC.

A luminous flux diameter upon irradiation of the magnetooptic element 5 is adjusted to match a size of the magnetooptic element 5 by an optical element, such as a lens, which is not illustrated in FIG. 5. Further, the optical system from the magnetooptic element 5 to the detector 12 is a telecentric optical system.

Figure 6:
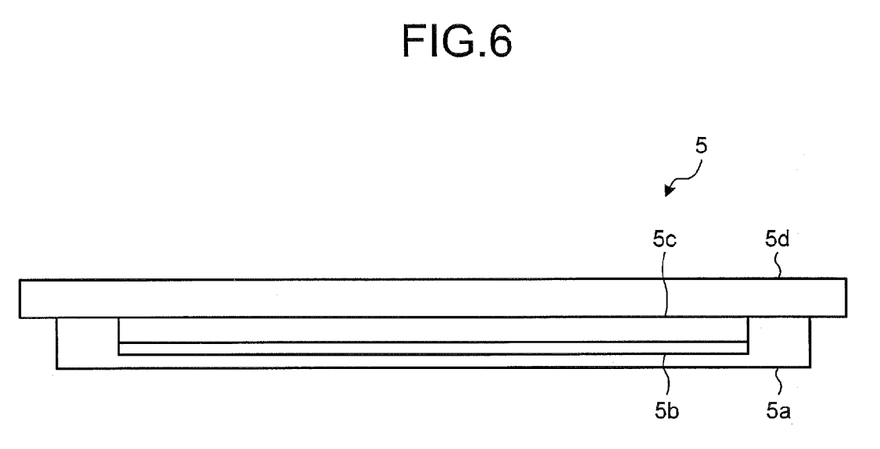
FIG. 6 is a cross section diagram illustrating an example of a configuration of a magnetooptic element.

FIG. 6 is a cross section diagram illustrating an example of a configuration of the magnetooptic element 5. As illustrated in FIG. 6, the magnetooptic element 5 is configured of, in order from a direction facing the steel sheet "S", a protective film 5a, a reflective film 5b, a magnetooptic film 5c, and a substrate 5d. The magnetooptic film 5c preferably has a composition including magnetic garnet. The polarized light, with which this magnetooptic element 5 is irradiated, is incident on the substrate 5d, transmitted through the magnetooptic film 5c, reflected by the reflective film 5b, and thereafter transmitted through the magnetooptic film 5c and the substrate 5d again to be emitted from the magnetooptic element 5.

Figure 7:
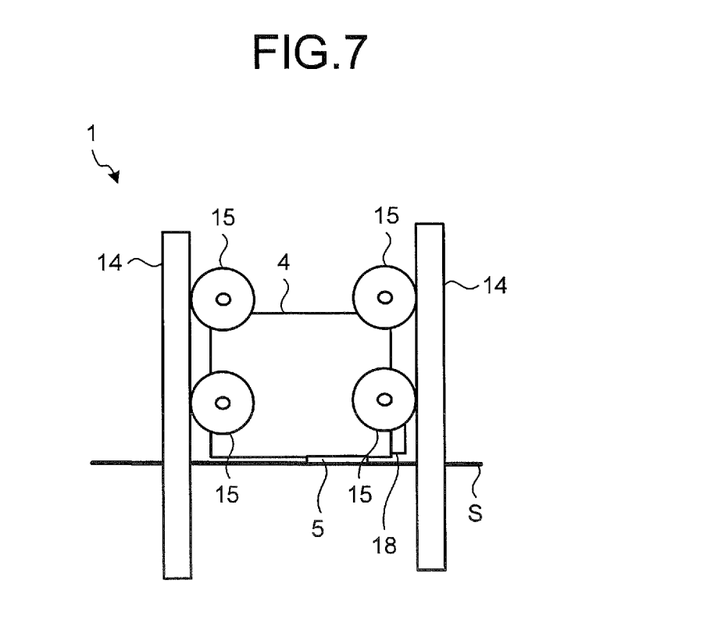
FIG. 7 is a side view of a drive mechanism of the electron gun abnormality detecting device.
Figure 8:
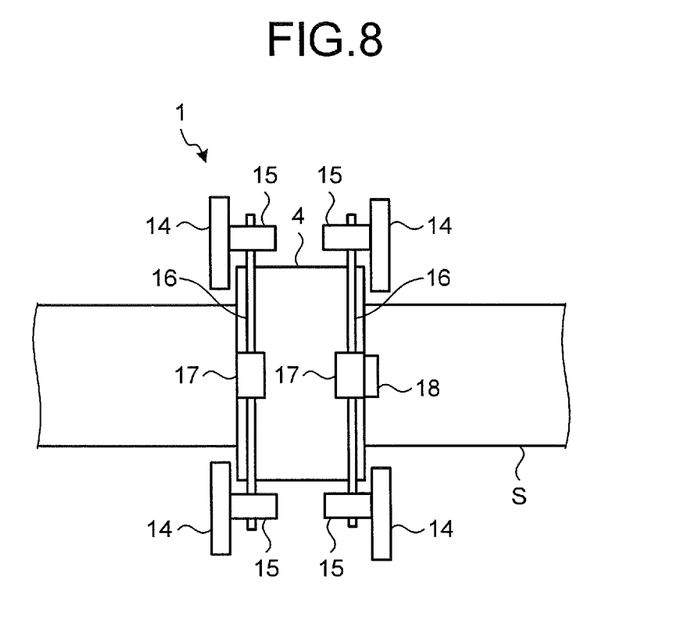
FIG. 8 is a top view of the drive mechanism of the electron gun abnormality detecting device.

FIG. 7 and FIG. 8 are diagrams of a schematic configuration illustrating a drive system of the electron gun abnormality detecting device 1 according to the embodiment of the present invention. FIG. 7 is a side view of a drive mechanism of the electron gun abnormality detecting device 1 and FIG. 8 is a top view of the drive mechanism of the electron gun abnormality detecting device 1.

As illustrated in FIG. 7 and FIG. 8, in the electron gun abnormality detecting device 1 according to the embodiment of the present invention, the inspection unit 4 is able to move up and down along rails 14 vertically placed on both sides of the manufacturing line of the steel sheet "S". The inspection unit 4 is arranged movably on the rails 14 by wheels 15, and a motor 17 is provided on each of axles 16 of the wheels 15. The inspection unit 4 moves up and down along the rails 14 by rotational drive of the motors 17.

As illustrated in FIG. 7 and FIG. 8, the inspection unit 4 includes a proximity sensor 18. The proximity sensor 18 is a sensor for measuring a distance between the inspection unit 4 and the surface of the steel sheet "S". In the electron gun abnormality detecting device 1 according to the embodiment of the present invention, when the inspection unit 4 is lowered to cause the magnetooptic element 5 to come into contact with the surface of the steel sheet "S", the inspection unit 4 is lowered at a low speed near the steel sheet "S" such that the surface of the steel sheet "S" and the magnetooptic element 5 are not damaged by colliding each other. The proximity sensor 18 detects a height where the lowering speed of the inspection unit 4 is to be changed to the low speed.

The drive mechanism illustrated in FIG. 7 and FIG. 8 is just an example applicable to the electron gun abnormality detecting device 1 according to the embodiment of the present invention. Therefore, not being limited to the drive mechanism illustrated in FIG. 7 and FIG. 8, another mechanism, such as that of winch type may be used. Further, the drive mechanism illustrated in FIG. 7 and FIG. 8 drives the inspection unit 4 integrally therewith, but a configuration, which drives only some of the structural elements included in the inspection unit 4, for example, the magnetooptic element 5 and the holder 6, may be used.

[Electron Gun Abnormality Detecting Method]

Hereinafter, an electron gun abnormality detecting method according to the embodiment of the present invention will be described. In the description below, the electron gun abnormality detecting method according to the embodiment of the present invention will be described with reference to the drawings of the configuration of the electron gun abnormality detecting device according to the embodiment of the present invention and the like, but, the electron gun abnormality detecting method according to the embodiment of the present invention is not limited by the configuration illustrated in these drawings.

Figure 9:
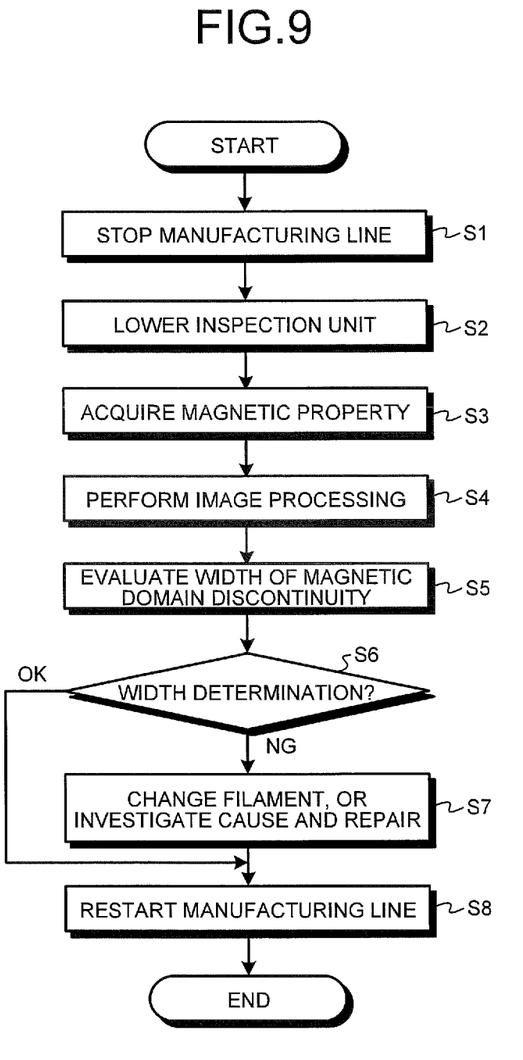
FIG. 9 is a flow chart illustrating an electron gun abnormality detecting method according to the embodiment of the present invention.

FIG. 9 is a flow chart illustrating the electron gun abnormality detecting method according to the embodiment of the present invention. As illustrated in FIG. 9, the electron gun abnormality detecting method according to the embodiment of the present invention is performed in a state where the manufacturing line of the steel sheet "S" has been stopped (Step S1). Efficient timing to stop this manufacturing line is at a stop upon joining of coils of steel sheet "S", for example, but the timing may be at a stop separately set for detecting an abnormality in the electron guns.

Next, the inspection unit 4 of the electron gun abnormality detecting device 1 is lowered towards the surface of the steel sheet "S" (Step S2). By the inspection unit 4 being lowered towards the surface of the steel sheet "S", the magnetooptic element 5 contacts the inspection region "R" of the steel sheet "S" and the magnetic domain structure of the steel sheet "S" is transferred to the magnetooptic film 5c of the magnetooptic element 5.

Thereafter, a magnetic property of the steel sheet "S" is acquired (Step S3). That is, by the magnetooptic element 5 being irradiated with linearly polarized light, and the linearly polarized light passing through the magnetooptic film 5c of the magnetooptic element 5, rotation of the polarization plane due to Faraday effect occurs and the inspection unit 4 detects the magnetic domain structure of the steel sheet "S" by this rotation of the polarization plane.

The detected magnetic domain structure of the steel sheet "S" is subjected to appropriate image processing by the separate image processing means 13, such as the PC (Step S4). The image processing means 13 performs evaluation of the magnetic domain discontinuity for a visualized image of the magnetic domain structure of the steel sheet "S" and detects a boundary between a magnetic domain and a magnetic domain discontinuity. Further, the image processing means 13 performs evaluation of the width of the magnetic domain discontinuity, based on the size of the magnetooptic element 5, a magnification of the measurement optical system, a distance to the steel sheet "S", and the like (Step S5).

Thereafter, the control means 1b performs determination of the width of the magnetic domain discontinuity (Step S6). This determination of the width of the magnetic domain discontinuity is not only determination of whether or not the width of the magnetic domain discontinuity is within a predetermined width range but also determination of whether or not displacement of the magnetic domain discontinuity has occurred. That is, as illustrated in FIG. 3 and FIG. 4, abnormalities in the electron guns 3 appear in different ways in the magnetic domain discontinuity "L" in the inspection region "R". Accordingly, if the widths of the magnetic domain discontinuity "L" of the top half of the inspection region "R" and of the magnetic domain discontinuity "L" of the bottom half of the inspection region "R" are different from each other, the control means 1b presumes that the filament of the electron gun 3 has deteriorated, and if the positions of the magnetic domain discontinuity "L" of the top half of the inspection region "R" and of the magnetic domain discontinuity "L" of the bottom half of the inspection region "R" are displaced from each other, the control means 1b presumes that displacement in the mechanical position of the electron gun 3 or deviation in timing to perform irradiation with the election beam from the electron gun 3 has occurred.

If the determination of the width of the magnetic domain discontinuity by the control means 1b indicates abnormality (step S6; NG), changing of the filament of the electron gun 3, or investigation of another cause and repair thereof is/are performed (Step S7), and the manufacturing line of the steel sheet "S" is restarted (Step S8).

On the contrary, if the determination of the width of the magnetic domain discontinuity by the control means 1b does not indicate abnormality (Step S6; OK), the manufacturing line of the steel sheet "S" that has been stopped is restarted (Step S8).

The control means 1b preferably has a control process of not changing the filament by issuing an order to increase or decrease the electron beam power of the electron gun 3 of the magnetic domain refining device 2 if the width of the magnetic domain discontinuity is not within the predetermined range and the control means 1b is preferably provided with means for decreasing the number of times the filament of the electron gun 3 is changed.

[Working Example]

Figure 10:
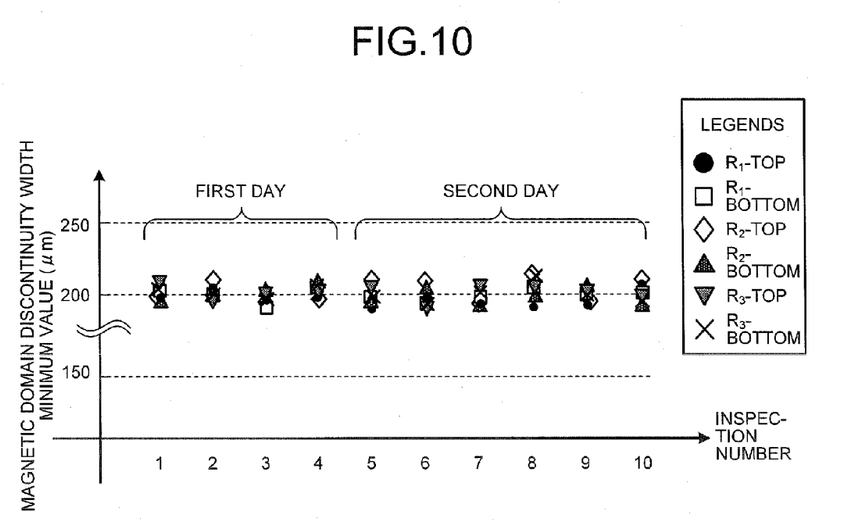
FIG. 10 is a graph of minimum values of width of a magnetic domain discontinuity detected by the electron gun abnormality detecting method according to the embodiment of the present invention.
Figure 11:
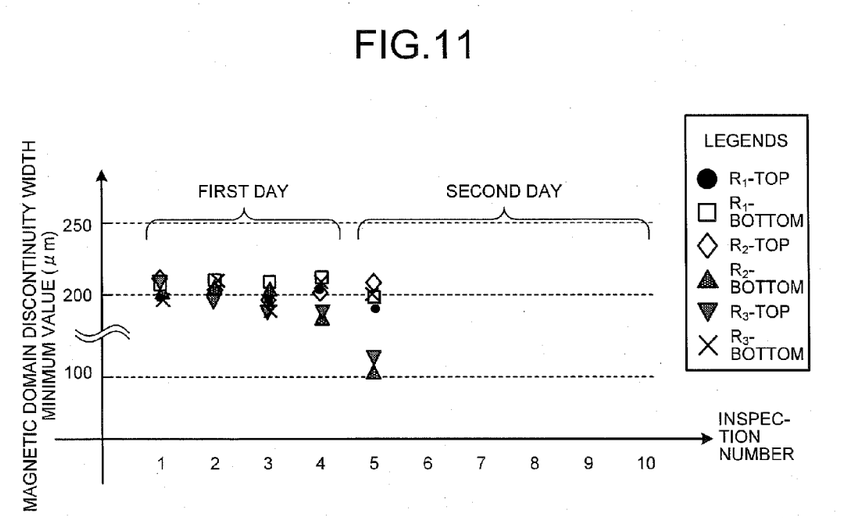
FIG. 11 is a graph of minimum values of the width of the magnetic domain discontinuity detected by the electron gun abnormality detecting method according to the embodiment of the present invention.

Next, an operation example of a manufacturing line for which a process of detecting an abnormality in the electron guns 3 of the magnetic domain refining device 2 is performed by the electron gun abnormality detecting method according to the embodiment of the present invention will be described. FIG. 10 and FIG. 11 are graphs of minimum values of the width of the magnetic domain discontinuity detected by the electron gun abnormality detecting method according to the embodiment of the present invention.

FIG. 10 illustrates inspection results for two days of a manufacturing line, and FIG. 11 illustrates inspection results for two days of the manufacturing line after three months from the detection of FIG. 10. The inspection is performed upon the stop when the coil of steel sheet "S" in the manufacturing line is switched over. In line with the assignment of the symbols in FIG. 2, as illustrated by legends in the graphs of FIG. 10 and FIG. 11, the minimum values of the width of the magnetic domain discontinuity in the top half of the inspection region $R_1$ are represented by filled circles, the minimum values of the width of the magnetic domain discontinuity in the bottom half of the inspection region $R_1$ are represented by open squares, the minimum values of the width of the magnetic domain discontinuity in the top half of the inspection region $R_2$ are represented by open diamonds, the minimum values of the width of the magnetic domain discontinuity of the bottom half of the inspection region $R_2$ are represented by filled triangles, the minimum values of the width of the magnetic domain discontinuity in the top half of the inspection region $R_3$ are represented by filled inverted triangles, and minimum values of the width of the magnetic domain discontinuity in the bottom half of the inspection region $R_3$ are represented by crosses.

As illustrated in FIG. 10, if the electron guns 3 of the magnetic domain refining device 2 are normal, in the top halves and bottom halves of all of the inspection regions $R_1$, the minimum values of the width of the magnetic domain discontinuity are around 200 µm. On the contrary, in the inspection of the fifth time illustrated in FIG. 11, the minimum value of the width of the magnetic domain discontinuity in the bottom half of the inspection region $R_2$ indicated by the filled triangle and the minimum value of the width of the magnetic domain discontinuity in the top half of the inspection region $R_3$ indicated by the filled inverted triangle have decreased to about 100 µm. Therefore, by the inspection result of the fifth time illustrated in FIG. 11, occurrence of an abnormality in the electron gun $3_c$ of the magnetic domain refining device 2 is detected. In particular, by this inspection result, the filament of the electron gun $3_c$ of the magnetic domain refining device 2 is determined to have been deteriorated.

In the above described working example, although the occurrence of an abnormality is determined by the minimum values of the width of the magnetic domain discontinuity in the inspection regions, occurrence of an abnormality may be determined by using an average value, a variance, or the like of widths of the magnetic domain discontinuity.

As described above, the electron gun abnormality detecting device 1 of the present invention is the electron gun abnormality detecting device 1 that detects an abnormality in the electron guns 3 of the magnetic domain refining device 2 for an electrical steel sheet, the magnetic domain refining device 2 including the plurality of electron guns $3_a$, $3_b$, $3_c$, and $3_d$, and the electron gun abnormality detecting device 1 includes: the magnetooptic element, which contacts with and separates from the inspection regions $R_1$, $R_2$, and $R_3$ set to include boundaries of the magnetic domain discontinuity "L" generated by the plurality of electron guns $3_a$, $3_b$, $3_c$, and $3_d$ irradiating the surface of the electrical steel sheet with the electron beams, and which is able to detect the magnetic domain structure of the steel sheet "S" in the inspection regions $R_1$, $R_2$, and $R_3$ as an optical property; the light source 7, which irradiates the magnetooptic element 5 with linearly polarized light; and the detector 12, which detects the polarized light rotated by the magnetic domain structure of the steel sheet "S" transferred to the magnetooptic element 5, and thus by the inspection in the inspection regions $R_1$, $R_2$, and $R_3$, less than the number of the electron guns $3_a$, $3_b$, $3_c$, and $3_d$ installed in the magnetic domain refining device 2, an abnormality in the electron guns $3_a$, $3_b$, $3_c$, and $3_d$ is able to be detected.

Further, the magnetooptic element 5 according to the embodiment of the present invention is configured of, in the order from the direction facing the steel sheet "S", the protective film 5a, the reflective film 5b, the magnetooptic film 5c, and the substrate 5d, and linearly polarized light is incident thereon from the substrate 5d side and reflected by the reflective film 5b, and thus, Faraday effect is able to be obtained doubly by the incident linearly polarized light traveling back and forth through the magnetooptic film 5c. Moreover, the magnetooptic film 5c preferably has the composition including magnetic garnet.

INDUSTRIAL APPLICABILITY

As described above, an electron gun abnormality detecting device and an electron gun abnormality detecting method are applicable to a process of detecting an abnormality in electron guns, which generate electron beams, of a magnetic domain refining device.

REFERENCE SIGNS LIST

1 Electron gun abnormality detecting device
1b Control means
2 Magnetic domain refining device
3, $3_a$, $3_b$, $3_c$, $3_d$ Electron gun
4 Inspection unit
5 Magnetooptic element
5a Protective film
5b Reflective film
5c Magnetooptic film
5d Substrate
6 Holder
7 Light source
8 Collimator lens
9 Polarizer
10 Half mirror
11 Analyzer
12 Detector
13 Image processing means
14 Rail
15 Wheel
16 Axle
17 Motor
18 Proximity sensor

The invention claimed is:
1. An electron gun abnormality detecting device for detecting an abnormality in electron guns of a magnetic domain refining device for an electrical steel sheet, the magnetic domain refining device including at least a first electron gun and a second electron gun, and the electron gun abnormality detecting device comprising:

a magnetooptic element configured to contact with and separate from an inspection region set to include a boundary between a magnetic domain discontinuity generated by irradiation of a surface of the electrical steel sheet with an electron beam by the first electron gun and a magnetic domain discontinuity generated by irradiation thereof with an electron beam by the second electron gun, and configured to detect a steel sheet magnetic domain structure in the inspection region as an optical property;

a light source configured to irradiate the magnetooptic element with linearly polarized light; and a detector configured to detect polarized light rotated by the steel sheet magnetic domain structure transferred to the magnetooptic element.

2. The electron gun abnormality detecting device according to claim 1, wherein
the magnetooptic element is configured of, in order from a direction facing the steel sheet, a protective film, a reflective film, a magnetooptic film and a substrate, and
the linearly polarized light is incident from a side of the substrate and is reflected by the reflective film.

3. The electron gun abnormality detecting device according to claim 2, wherein the magnetooptic film has a composition including magnetic garnet.

4. The electron gun abnormality detecting device according to claim 1, further comprising a polarizer, a half mirror and an analyzer, wherein a light ray emitted from the light source is propagated through and in the order of, the polarizer, the half mirror, the magnetooptic element, the half mirror, the analyzer and the detector.

5. The electron gun abnormality detecting device according to claim 4, further comprising a drive mechanism driving an inspection unit accommodating the light source, the polarizer, the half mirror, the magnetooptic element, the analyzer and the detector, and
wherein the inspection region of the steel sheet and the magnetooptic element are caused to contact with and separate from each other.

6. The electron gun abnormality detecting device according to claim 1, wherein the number of the inspection areas arranged in a width direction of the steel sheet is one less than the number of the electron guns included in the magnetic domain refining device.

7. An electron gun abnormality detecting method of detecting an abnormality in electron guns of a magnetic domain refining device including at least a first electron gun and a second electron gun, the electron gun abnormality detecting method including:
a contacting step of contacting, with a steel sheet, a magnetooptic element that detects a magnetic domain structure of the steel sheet as an optical property at an inspection region set to include a boundary between a magnetic domain discontinuity generated by irradiation with an electron beam by the first electron gun and a magnetic domain discontinuity generated by irradiation with an electron beam by the second electron gun;
an irradiating step of irradiating the magnetooptic element with linearly polarized light;
a detecting step of detecting a rotation of a polarization plane of the linearly polarized light reflected by the magnetooptic element;
a measuring step of measuring the magnetic domain structure of the steel sheet from the rotation of the polarization plane; and
a separating step of separating the magnetooptic element from the steel sheet.

8. The electron gun abnormality detecting method according to claim 7, wherein
the magnetooptic element is configured of, in order from a direction facing the steel sheet, a protective film, a reflective film, a magnetooptic film, and a substrate, and
the linearly polarized light is incident from a side of the substrate and is reflected by the reflective film.

9. The electron gun abnormality detecting method according to claim 8, wherein the magnetooptic film has a composition including magnetic garnet.

10. The electron gun abnormality detecting device according to claim 2, further comprising a polarizer, a half mirror and an analyzer, wherein a light ray emitted from the light source is propagated through and in the order of, the polarizer, the half mirror, the magnetooptic element, the half mirror, the analyzer and the detector.

11. The electron gun abnormality detecting device according to claim 3, further comprising a polarizer, a half mirror and an analyzer, wherein a light ray emitted from the light source is propagated through and in the order of, the polarizer, the half mirror, the magnetooptic element, the half mirror, the analyzer and the detector.

12. The electron gun abnormality detecting device according to claim 10, wherein by the electron gun abnormality detecting device further comprising an inspection unit accommodating the light source, the polarizer, the half mirror, the magnetooptic element, the analyzer and the detector, the inspection region of the steel sheet and the magnetooptic element are caused to contact with and separate from each other.

13. The electron gun abnormality detecting device according to claim 11, wherein by the electron gun abnormality detecting device further comprising an inspection unit accommodating the light source, the polarizer, the half mirror, the magnetooptic element, the analyzer and the detector, the inspection region of the steel sheet and the magnetooptic element are caused to contact with and separate from each other.

14. The electron gun abnormality detecting device according to claim 2, wherein the number of the inspection areas arranged in a width direction of the steel sheet is one less than the number of the electron guns included in the magnetic domain refining device.

15. The electron gun abnormality detecting device according to claim 3, wherein the number of the inspection areas arranged in a width direction of the steel sheet is one less than the number of the electron guns included in the magnetic domain refining device.

16. The electron gun abnormality detecting device according to claim 4, wherein the number of the inspection areas arranged in a width direction of the steel sheet is one less than the number of the electron guns included in the magnetic domain refining device.

17. The electron gun abnormality detecting device according to claim 5, wherein the number of the inspection areas arranged in a width direction of the steel sheet is one less than the number of the electron guns included in the magnetic domain refining device.

18. The electron gun abnormality detecting device according to claim 10, wherein the number of the inspection areas arranged in a width direction of the steel sheet is one less than the number of the electron guns included in the magnetic domain refining device.

19. The electron gun abnormality detecting device according to claim 11, wherein the number of the inspection areas arranged in a width direction of the steel sheet is one less than the number of the electron guns included in the magnetic domain refining device.

20. The electron gun abnormality detecting device according to claim 12, wherein the number of the inspection areas arranged in a width direction of the steel sheet is one less than the number of the electron guns included in the magnetic domain refining device.

21. The electron gun abnormality detecting device according to claim 13, wherein the number of the inspection areas arranged in a width direction of the steel sheet is one less than the number of the electron guns included in the magnetic domain refining device.

* * * * *